United States Patent
Li et al.

(10) Patent No.: US 7,684,853 B2
(45) Date of Patent: Mar. 23, 2010

(54) METHOD AND APPARATUS FOR SUPPRESSING POWER FREQUENCY COMMON MODE INTERFERENCE

(75) Inventors: Shunan Li, Shenzhen (CN); Xiaoyu Wu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 985 days.

(21) Appl. No.: 11/316,190

(22) Filed: Dec. 22, 2005

(65) Prior Publication Data

US 2007/0087703 A1    Apr. 19, 2007

(30) Foreign Application Priority Data

Oct. 19, 2005    (CN)    .................... 2005 1 0100533

(51) Int. Cl.
  *A61B 5/04*    (2006.01)
(52) U.S. Cl. ..................................... 600/509
(58) Field of Classification Search ................. 128/901, 128/908; 600/509, 544; 607/63
  See application file for complete search history.

(56) References Cited

U.S. PATENT DOCUMENTS

| | | | | |
|---|---|---|---|---|
| 5,029,118 A | * | 7/1991 | Nakajima et al. | 702/195 |
| 5,482,036 A | * | 1/1996 | Diab et al. | 600/364 |
| 5,513,649 A | * | 5/1996 | Gevins et al. | 600/544 |
| 5,555,888 A | * | 9/1996 | Brewer et al. | 600/515 |
| 5,742,900 A | * | 4/1998 | Arnstein et al. | 455/296 |
| 5,966,684 A | * | 10/1999 | Richardson et al. | 702/191 |
| 6,297,661 B1 | | 10/2001 | Chen | |
| 6,870,109 B1 | | 3/2005 | Villarreal | |
| 2003/0073916 A1 | * | 4/2003 | Yonce | 600/509 |
| 2004/0097802 A1 | | 5/2004 | Cohen | |

FOREIGN PATENT DOCUMENTS

| | | |
|---|---|---|
| CN | 87102381 A | 10/1988 |
| CN | 2394572 Y | 9/2000 |
| CN | 1475811 A | 2/2004 |
| CN | 1611185 A | 5/2005 |
| JP | 1227740 A | 9/1989 |
| JP | 200235950 A | 2/2002 |
| JP | 2004117260 A | 4/2004 |

* cited by examiner

*Primary Examiner*—Carl H Layno
*Assistant Examiner*—Gary A Porter, Jr.
(74) *Attorney, Agent, or Firm*—Kory D. Christensen; Stoel Rives LLP

(57) ABSTRACT

A method for suppressing power frequency common mode interference comprises the following steps of: receiving a bioelectrical signal from a living body on examination by phase compensating and processing circuitry; analyzing the characteristics of the bioelectrical signal and determining a phase compensation amount by the phase compensating and processing circuitry; performing a corresponding time delay processing on an amplified signal outputted by the driving circuit; and providing the delay signal to the living body on examination.

10 Claims, 3 Drawing Sheets

METHOD AND APPARATUS FOR SUPPRESSING POWER FREQUENCY COMMON MODE INTERFERENCE

This application claims the benefit of Chinese Patent Application No. 200510100533.8, filed Oct. 19, 2005, the contents of which are incorporated herein by reference in their entirety.

FIELD OF THE INVENTION

The present invention relates to an anti-interference technique used in detection of bioelectrical signals, more specifically, to an improvement and a method of a driving circuit for suppressing power frequency common mode interference.

DESCRIPTION OF THE RELATED ART

Power frequency (industrial frequency) interference widely exists during the measurement of the bioelectrical signals, and is generally caused by indoor illumination or power equipments. The interference frequencies are various, generally 50 Hz or 60 Hz, depending on the frequencies of the power grid in different countries. Since such frequencies normally fall into the frequency range of the bioelectrical signals themselves, such as electrocardiograph (ECG) signal and electroencephalogram (EEG) signal, it is critically important to improve the anti-interference capability of the equipment for acquiring high-quality bioelectrical signals.

Presently, a driving circuit as shown in FIG. 1 is widely employed in the power frequency interference suppressing technique adopted in the measurement of the bioelectrical signals. For example, the circuit is connected but not limited to a right leg of a human body. The circuit includes an auxiliary amplifier $A_3$, an output terminal of which is connected to the right leg via a resistor $R_0$, and an input terminal of which receives power frequency interference common mode voltage from the human body (for example, in the ECG detection shown in FIG. 1a, amplifiers $A_1$ and $A_2$ acquire a pair of differential detection signal from the human body, and the common mode voltage can be outputted from the series connection point of the two resistors connected in series between the differential signals). Since the right leg is not in contact with the ground directly, the displacement current of the human body will flow to the resistor $R_0$ and the output terminal of the auxiliary amplifier. Here, the resistor $R_0$ has a protecting function, that is, once a high voltage exists between the patient and the ground, the auxiliary amplifier $A_3$ is in the saturation state which is equivalent as connecting the ground, and the resistor $R_0$ perform a function of limiting current to protect the human body.

The common mode voltage upon the auxiliary amplifier being in the saturation state may be calculated from an equivalent circuit of the right leg driving circuit shown in FIG. 1b. Let the common mode gain of the high impedance input stage is 1 and the voltage of the output terminal of the auxiliary amplifier is $V_0$, then in the inverting terminal of the auxiliary amplifier $$\frac{2V_{cm}}{R_a} + \frac{V_0}{R_F} = 0 \quad (2\text{-}1)$$

and then $$V_0 = -\frac{2R_F V_{cm}}{R_a} \quad (2\text{-}2)$$

Since $V_{cm} = I_d R_0 + V_0$, then $$V_{cm} = \frac{I_d R_0}{1 + \frac{2R_F}{R_a}} \quad (2\text{-}3)$$

Thus, $|V_{cm}|$ can be minimized by both using the right leg driving circuit and increasing $R_F/R_a$.

However, in a practical ECG signal measurement environment, a low-pass filter is normally added in the input stage of the driving circuit for filtering out high-frequency interference. At the same time, the actual equivalent circuit of the right leg driving circuit is the circuit shown in FIG. 2, since there are electrostatic coupling capacitances existing among the human body, measuring instruments and power lines. In the equivalent circuit, $C_s$ is distributed capacitance between a common mode amplifier and the ground, $C_b$ is distributed capacitance between the human body and the ground, G is an inverting amplifying factor, $R_{el}$ is electrode impedance, and $R_0$ is a current limiting resistor. A phase shift of 180° (wherein, "H" shown in FIG. 2 denotes a transfer function, $$H = \frac{1}{1 + \frac{G}{2\pi B}s})$$

is introduced in the closed-loop system.

Amplifiers A1 and A2 achieve unity gain, and do not produce phase shifts in interested frequency domains. However, the auxiliary amplifier A3 has a pole at the frequency f=B/G (wherein B is a gain bandwidth). Meanwhile, the low-pass filter formed by a second order RC network may change the phase shift of the system (the figure ignores the electrode capacitance). As no way to determine $R_{el}$ and $C_b$, the accurate position of the pole cannot be determined, such that the pole canceling is difficult to achieve. In order to ensure the stability of the system, the measures of lowering a corner frequency and adding a feedback capacitance are usually employed. However, the output signal of the right leg driving and amplifying circuit is not in opposite phase with the common mode signal completely due to the effect of the feedback capacitance.

Take an application circuit of the right leg driving circuit shown in FIG. 3 as an example, wherein its frequency characteristic is shown in FIG. 4. It can be seen that the phase of the feedback signal outputted from the circuit is not in opposite phase by 180°, but by 126° at the interference frequency of 50 Hz. Therefore, the actual effect of suppressing power frequency common mode interference cannot reach the level of the theoretical analysis. Furthermore, the circuit delay of the actual measuring apparatus is affected by the parameters of circuit components, operational amplifiers and cables. In the process of measurement, the human body, measurement environment and measuring apparatus constitute a complicated measuring system, and the impedance of the human body, skin electrode impedance and electrostatic coupling capacitance will make the measuring-system transfer function more complicated, wherein the human body is in the important section within the feedback circuit, thus the parameters of the human body become critical factors to the changing of the system transfer function. However, since the individual differences among human bodies are unpredictable, the anti-interference capability of the ECG measuring system is of indeterminacy.

In conclusion, the disadvantages of the above-mentioned related technique are the phase of the feedback signal outputted by the driving circuit is unable to reach the complete opposite phase upon measuring bioelectrical signals each time, because the frequency characteristic of the hardware circuit is constant, while the system transfer function is uncertain upon practical measurements, thus the system capability of suppressing power frequency interference is reduced.

SUMMARY OF THE INVENTION

In view of above-mentioned disadvantages of prior art, the object of this invention is to provide a method and apparatus for suppressing the power frequency common mode interference, which is used in a bioelectrical signal measuring system. By improving the driving circuit through auto-performing phase compensation to make the amplified and outputted feedback signal in opposite phase by 180° with the power frequency common mode interference signal, the system capability of suppressing power frequency common mode interference is thus getting improved.

To resolve the above technical problems, the basic idea of this invention is to provide an embedded system circuit in the driving circuit (for example, the driving circuit is connected with a right leg, but not limited to the right leg), in which it receives an amplified signal originally outputted by the driving circuit, collects a bioelectrical signal, and further analyzes the bioelectrical signal to determine the auto-compensation amount of the phase of the original amplified signal, so the compensated amplified signal is able to feedback to the right leg for offsetting the power frequency common mode interference signal. By this method the capability of suppressing interference obtains improvement and facilitates the measuring system to collect the high qualified ECG signal. Besides, if providing a switching and selecting means, the embedded system circuit for compensating phases is getting further controlled as to decide whether utilize it or not.

In the first aspect of the invention, an apparatus for suppressing power frequency common mode interference and used in a bioelectrical signal measuring system is provided, which comprises: a common mode interference signal extracting circuit; and a driving circuit connected to the extracting circuit, wherein the driving circuit changes a phase of a common mode interference signal and amplifies the common mode interference signal, so as to output two-way amplified signals, and one amplified signal is selectively outputted to a living body on examination. More particularly, the apparatus further includes phase compensating and processing means for receiving both a bioelectrical signal from the living body on examination and the other amplified signal outputted from the driving circuit, determining a phase compensation amount of the other amplified signal outputted from the driving circuit according to a characteristic value of the power frequency interference in the bioelectrical signal so as to phase-compensate the other amplified signal outputted from the driving circuit, and selectively outputting the phase-compensated amplified signal to the living body on examination.

In the above-described solution, the phase compensating and processing means includes: at least one A/D converter for converting the bioelectrical signal and the other amplified signal outputted from the driving circuit into digital signals respectively and supplying the digital signals to a microprocessor, which determines the phase compensation amount of the other amplified signal outputted from the driving circuit according to the characteristic value of the power frequency interference in the bioelectrical signal; and a D/A converter for receiving a signal from the microprocessor and converting the signal into an analog signal.

In the above-described solution, the apparatus further includes a low-pass filter, through which the phase-compensated amplified signal outputted by the phase compensating and processing means passes before being transmitted to the living body on examination.

In the above-described solution, the apparatus further includes switching and selecting means with two selecting terminals, one of which is connected to an output terminal of the driving circuit, the other of which is connected to an output terminal of the phase compensating and processing means, and the switching and selecting means selectively outputs the amplified signal outputted by the driving circuit and the phase-compensated amplified signal outputted by the phase compensating and processing means to the living body on examination.

In the above-described solution, the apparatus further includes switching and selecting means with two selecting terminals, one of which is connected to an output terminal of the driving circuit, the other of which is connected to an output terminal of the low-pass filter, and the switching and selecting means selectively outputs the amplified signal outputted by the driving circuit and the phase-compensated amplified signal outputted by the phase compensating and processing means to the living body on examination.

In the second aspect of this invention, a method for suppressing power frequency common mode interference is provided, which is used for suppressing interference of power frequency common mode signal during a bioelectrical signal measuring system detects bioelectrical signals, wherein the measuring system comprises a common mode interference signal extracting circuit and a driving circuit connected to the extracting circuit for both changing phases of a common mode interference signal and amplifying the common mode interference signal, characterized in that the method includes steps of:

A. providing phase compensating and processing means between the driving circuit and a living body on examination;

B. receiving an amplified signal outputted from the driving circuit and a bioelectrical signal from the living body on examination by the phase compensating and processing means;

C. analyzing the characteristic of the bioelectrical signal and determining a phase compensation amount of the amplified signal outputted from the driving circuit by the phase compensating and processing means, wherein the characteristic of the bioelectrical signal is represented by a characteristic value of the power frequency interference in the bioelectrical signal;

D. performing a corresponding time delay processing on the amplified signal outputted by the driving circuit;

E. selectively transmitting the delay signal to the living body on examination.

In the above-described solution, the step C includes steps of:

C1) initializing a system state value of the measuring system;

C2) extracting a characteristic value of the power frequency interference in a current system state of the measuring system;
C3) adding 1 to the system state value and extracting another characteristic value again;
C4) if the another characteristic value being decreased, it indicates the power frequency interference is reduced, thus the direction of the compensation is correct, then continuing the step C3) till the system state value becomes maximized; otherwise, it indicates the direction of the compensation is incorrect, then subtracting 1 from the system state value, and then an optimum system state value can be selected, wherein the system state value is integer and corresponds to one phase compensation state;
C5) setting the optimum system state value in the step 4) as a state value of the current system, to determine a corresponding phase compensation amount; the above steps C1)~C5) can be performed circularly.

In the above-described solution, the system state value ranges from [0, K], in which $$K = \text{int}\left(\frac{f_s}{200}\right) - 1,$$

int( ) denotes rounding operation, and $f_s$ denotes a sampling frequency of the bioelectrical signal.

In the above-described solution, the characteristic value of the power frequency interference refers to a sum of peak to peak values of the power frequency interference signal extracted from the bioelectric signal within a plurality of periods, which is calculated by steps of:
a) successively storing data of the bioelectrical signal sampled by the A/D converter into a predetermined data array;
b) receiving the data array by a digital band-pass filter so as to extract the power frequency interference signal and output related data;
c) detecting a maximum value and a minimum value of the output data within a period, so as to calculate the peak to peak value of the signal within the period;
d) calculating a sum of the peak to peak values in a plurality of adjacent periods so as to get the characteristic value of the power frequency interference.

In the above-described solution, the step D for performing a corresponding time delay processing on the amplified signal outputted by the driving circuit includes steps of:
D1) controlling the A/D converter by a microprocessor of the phase compensating and processing means, setting a sampling channel and a sampling frequency $f_s$, and sampling the amplified signal outputted by the driving circuit;
D2) creating a data array org_data[K+1], and successively storing amplified signal sampled by the A/D converter;
D3) determining a delay-output datum according to an optimum state value J of the current system, which corresponds an array element org_data[K−J] of the data array;
D4) converting the datum outputted at the sampling frequency $f_s$ into an analog signal by the D/A converter and then outputting the analog signal;
wherein $$K = \text{int}\left(\frac{f_s}{200}\right) - 1,$$

int ( ) denotes a rounding operation.

In the above-described solution, in the step D, the signal outputted by the driving circuit is transmitted to a delayer for performing a corresponding time delay processing, which is controlled by a microprocessor and whose delay time is adjustable.

With the above-described technical solutions, the automatic phase compensation of the driving circuit during the process of the measurement of the bioelectrical signals can be achieved by taking advantages of the characteristics of the close combination between the software and the hardware of the embedded system, as well as the stability of the analog circuit system and the phase-frequency characteristic of the circuit. The capability of the circuit suppressing power frequency common mode interference is getting improved, which contributes to the improvement of the quality of the sampled bioelectrical signals.

DETAILED DESCRIPTION OF THE PREFERRED EMBODIMENTS

Hereinafter, the preferred embodiments of this invention will be described in detail in conjunction with the figures.

Figure 1:
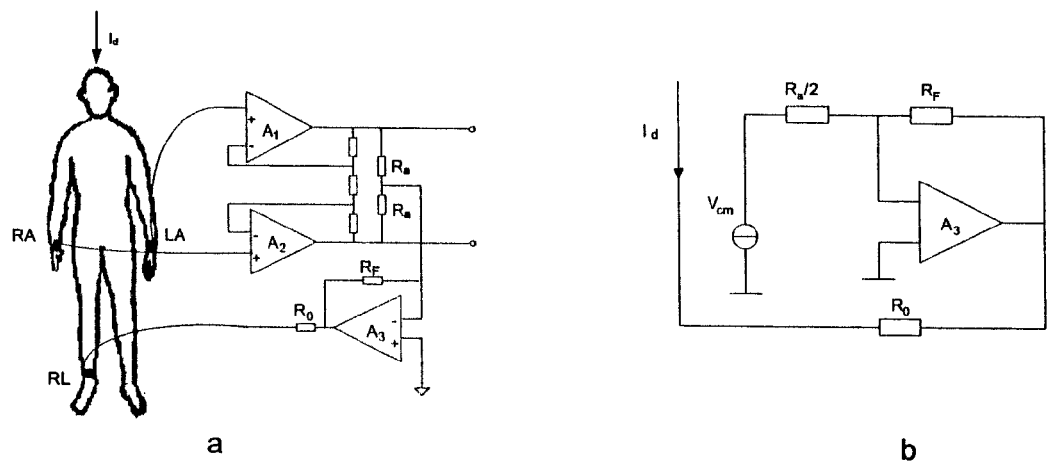
FIGS. 1a and 1b are schematic diagrams of the right leg driving circuit and the equivalent circuit thereof in the known ECG measuring system respectively.
Figure 2:
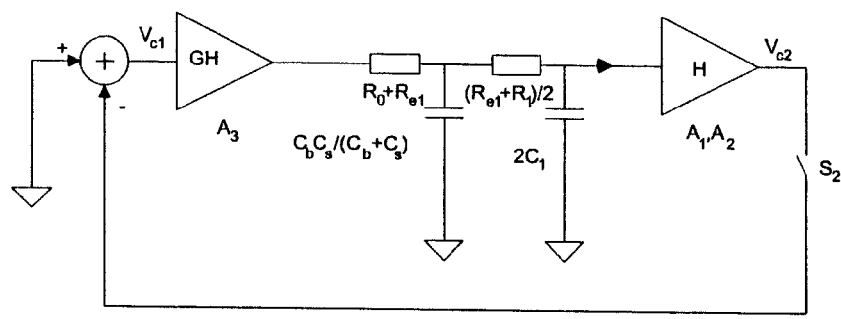
FIG. 2 is a schematic diagram of the actual equivalent circuit of the known right leg driving circuit.
Figure 3:
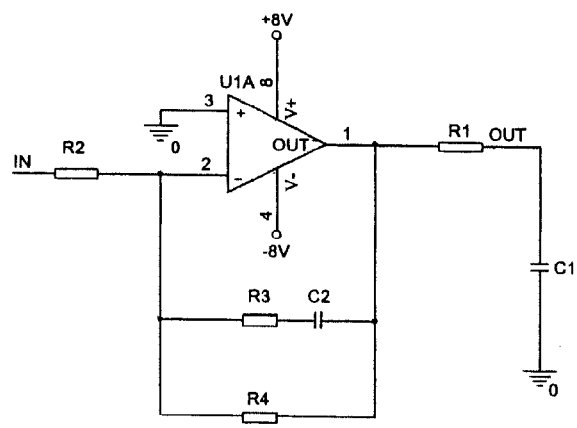
FIG. 3 shows one embodiment of the known right leg driving circuit.
Figure 4:
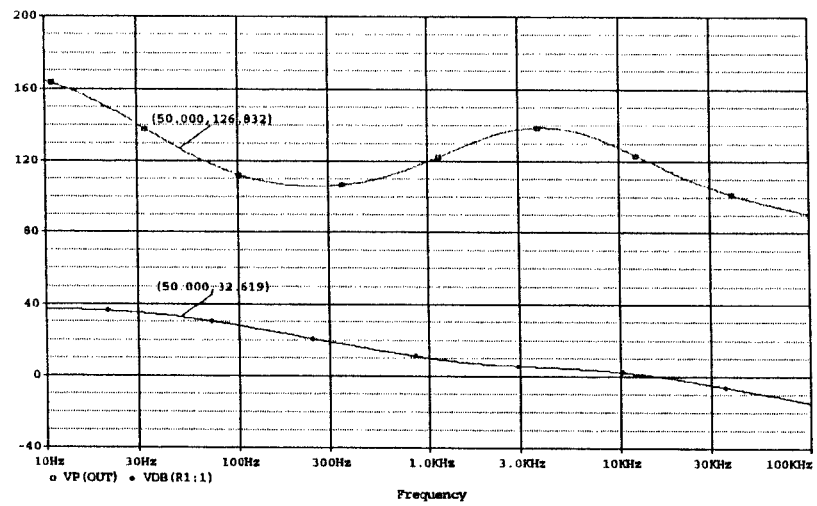
FIG. 4 is a frequency characteristic graph of the embodiment of the known right leg driving circuit.
Figure 5:
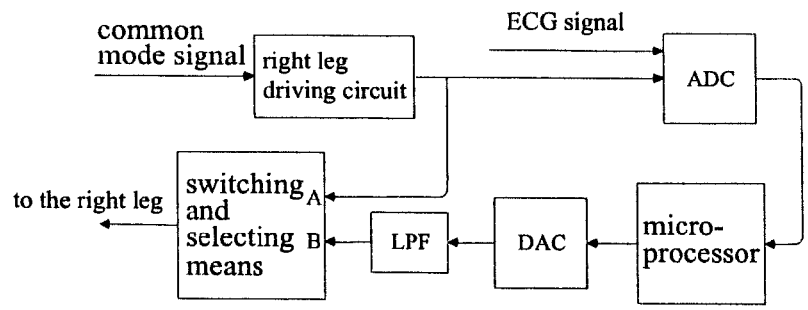
FIG. 5 is a block diagram of the improved right leg driving circuit for suppressing power frequency common mode interference according to the present invention.

FIG. 5 is a block diagram showing the principle of the improved (for example an ECG detection) driving circuit (for example right leg). A common signal extracted from a bio-electric signal (for example an ECG signal) by a common mode interference signal extracting circuit (known in the art and not shown) is provided into the right leg driving circuit, by which the phase of the common signal is changed and then amplified. The right leg driving circuit may output two-way amplified signals, in which one amplified signal which can be regarded as a feedback signal is selectively outputted to a living body on examination. In FIG. 5, phase compensating and processing means is provided for receiving both a bioelectrical signal from the living body on examination and the other amplified signal outputted from the driving circuit, determining a phase compensation amount of the other amplified signal outputted from the driving circuit according to a characteristic value of the power frequency interference in the bioelectrical signal so as to phase-compensate the other amplified signal outputted from the driving circuit, and selectively outputting the phase-compensated amplified signal to the living body on examination.

The phase compensating and processing means includes at least one A/D converter(ADC) for converting the bioelectrical signal and the other amplified signal outputted from the driving circuit into digital signals respectively and supplying the digital signals to a microprocessor, which determines the phase compensation amount of the other amplified signal outputted from the driving circuit according to the characteristic value of the power frequency interference in the bioelectrical signal; and a D/A converter (DAC) for receiving a signal from the microprocessor and converting the signal into an analog signal as an output of the phase compensating and processing means. The signal outputted by the phase compensating and processing means may be filtered via a low-pass filter (LPF) and then transmitted to the living body on examination. The A/D converter and D/A converter may be integrated into the microprocessor.

The improved circuit can also include switching and selecting means with two selecting terminals, one of which is connected to an output terminal of the driving circuit, the other of which is connected to an output terminal of the phase compensating and processing means, and the switching and selecting means selectively outputs the amplified signal outputted by the driving circuit and the phase-compensated amplified signal outputted by the phase compensating and processing means to the living body on examination (for example but not limited to the right leg). The switching and selecting means may select and output received signals by manual operation (for example a slide switch), or by the control of the system software through connecting a control terminal of the switching and selecting means to the microprocessor.

Figure 6:
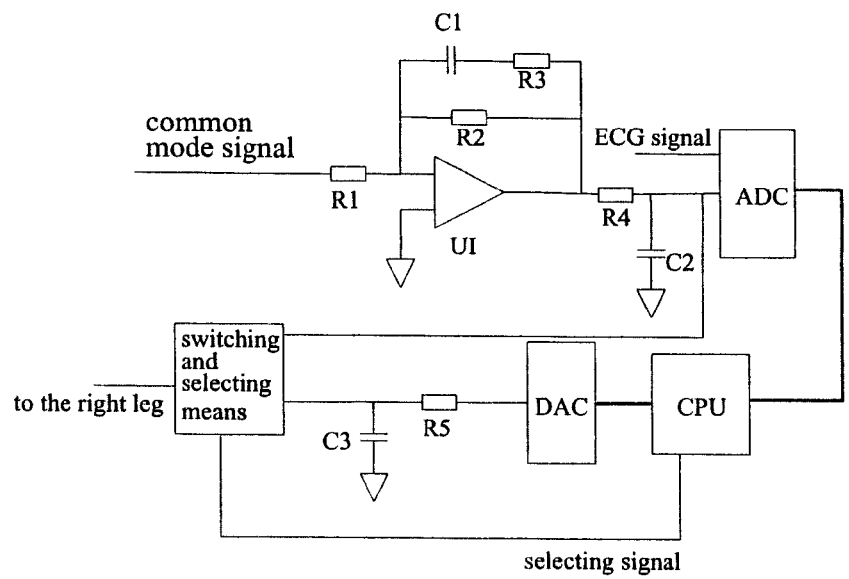
FIG. 6 is a concrete schematic diagram of the improved circuit according to the present invention.

FIG. 6 is a concrete schematic diagram of the above block diagram. The right leg driving circuit includes an inverting amplifier which is mainly composed of an amplifier integrated circuit U1 (for example but not limited to LM358), the gain of which can be set about −40 times (50 Hz). A capacitor C1 is used for decreasing high-frequency negative feedback gain, preventing high frequency self-excitation, and maintaining the stability of the feedback loop. A resistor R4 connected to an output terminal of the amplifier integrated circuit U1 is used for limiting current to ensure the amount of leakage current no more than 50 uA under a single failure mode. At the same time, the resistor R4 is also used for low-pass filtering together with a capacitor C2 which is connected to the other end of the resistor R4, so as to maintain the stability of the loop. The A/D converter may employ 8-bit or 12-bit analog-to-digital converter of which the sampling rate is not less than 1 kHz, for example but not limited to MAX1290. The D/A converter may correspond to the A/D converter, for example but not limited to MX7545A. The microprocessor fulfills the function of controlling and data processing, for example but not limited to MCS-51 family of one chip microprocessor or a CPU and the like.

The low-pass filter is mainly used for filtering out high frequency signals which is caused by the D/A conversion, and it may be achieved but not limited to a simple one-order RC filtering circuit, as shown by a resistor R5 and a capacitor C3 in the figure. The cutoff frequency of the filter is slightly less than a half of the sampling frequency. Filter circuits in other forms will not be further discussed here, since they are well-known in the art. The switching and selecting means in this embodiment may employ but not limited to MC14053 to be controlled by the microprocessor.

Since there is a phase leading between the phase shift of the original output signal of the driving circuit and the phase shift of 180° required by the negative feedback system, the signal can be phase-compensated by means of delay output. Therefore the method of the present invention for suppressing power frequency common mode interference may adopt follow steps based upon the above-mentioned hardware circuit or its equivalently transfer circuits:

A. providing phase compensating and processing means between the driving circuit and a living body on examination;

B. receiving an amplified signal outputted from the driving circuit and a bioelectrical signal from the living body on examination by the phase compensating and processing means;

C. analyzing the characteristic of the bioelectrical signal and determining a phase compensation amount of the amplified signal outputted from the driving circuit by the phase compensating and processing means, wherein the characteristic of the bioelectrical signal is represented by a characteristic value of the power frequency interference in the bioelectrical signal;

D. performing a corresponding time delay processing on the amplified signal outputted by the driving circuit;

E. selectively transmitting the delay signal to the living body on examination.

Assume the leading phase of the feedback signal outputted by the right leg driving circuit of the measuring system is θ, the system sampling frequency is $f_s$, then the time t for which the output of the driving signal needs to be delayed is:

$$t = \frac{\theta}{2\pi f_s} \qquad (4\text{-}1)$$

Since the signal outputted by the D/A conversion is a discrete signal, the real time for which the output is delayed is an integral multiple of the sampling period:

$$t_n = \frac{n}{f_s}, n = 0, 1, 2 \ldots \qquad (4\text{-}2)$$

Then, the corresponding delayed phase of the signal is:

$$\Delta\theta_n = 2\pi \frac{t_n}{T} = 100\pi \frac{n}{f_s}, n = 0, 1, 2 \ldots \qquad (4\text{-}3)$$

The compensation algorithm does not always make $\Delta\theta_n = \theta$, but can let $\Delta\theta_n$ approximately equal to θ, thus the leading phase of the system can be compensated to a certain extent, and the better signal quality can be achieved.

At the same time, it can be seen that the higher the sampling frequency is, the more $\Delta\theta_n$ approximates to θ and the better the compensation effect is.

Since the right leg driving circuit and the added phase compensating and processing means must constitute a negative feedback system, the leading phase of the original driving signal has a interval of [0, π/2). It is testified by experiments that the intensity of the power frequency interference signal has a unique minimum value when the driving signal is phase-compensated in this interval. Therefore, the optimum time $t_{opt}$ of the delay output can be found by use of the trend judgment, more specifically, by increasing the delay-output time, if the intensity of the power frequency interference decreases, it is recognized that the compensation is in a proper direction and then the delay time can be further increased. On the contrary, the delay time is considered as exceeding the optimum delay time, and the previous delay time can be regarded as the optimum delay time $t_{opt}$. In addition, the maximal delay time can be regarded as the optimum delay time $t_{opt}$, if the intensity of the power frequency interference signals continuously decreases in the interval of [0, π/2).

In the compensating phase interval of [0, π/2), n is an integer chosen from [0, K], in which $$K = \text{int}\left(\frac{f_s}{200}\right) - 1,$$

and int( ) denotes rounding operation. We call n as the system state value. The delay time of the output signal of the driving circuit corresponding to the system state value n is set as $t_n$. The intensity of the power frequency interference signals in the bioelectrical signals is represented with a characteristic value $F_n$. This characteristic value $F_n$ is defined as a sum of peak to peak values of the extracted power frequency interference signals within a plurality periods of interference signals. Thus, the step C includes following cycle processing procedures (as shown in FIG. 7):

C1) initializing a system state value of the measuring system;
C2) extracting a characteristic value of the power frequency interference in a current system state of the measuring system;
C3) adding 1 to the system state value and extracting another characteristic value again;
C4) if the another characteristic value being decreased, it indicates the power frequency interference is reduced, thus the direction of the compensation is correct, then continuing the step C3) till the system state value becomes maximized; otherwise, it indicates the direction of the compensation is incorrect, then subtracting 1 from the system state value, and then an optimum system state value can be selected, wherein the system state value is integer and corresponds to one phase compensation state;
C5) setting the optimum system state value in the step 4) as a state value of the current system, to determine a corresponding phase compensation amount;
the above steps C1)~C5) can be performed circularly.

Figure 7:
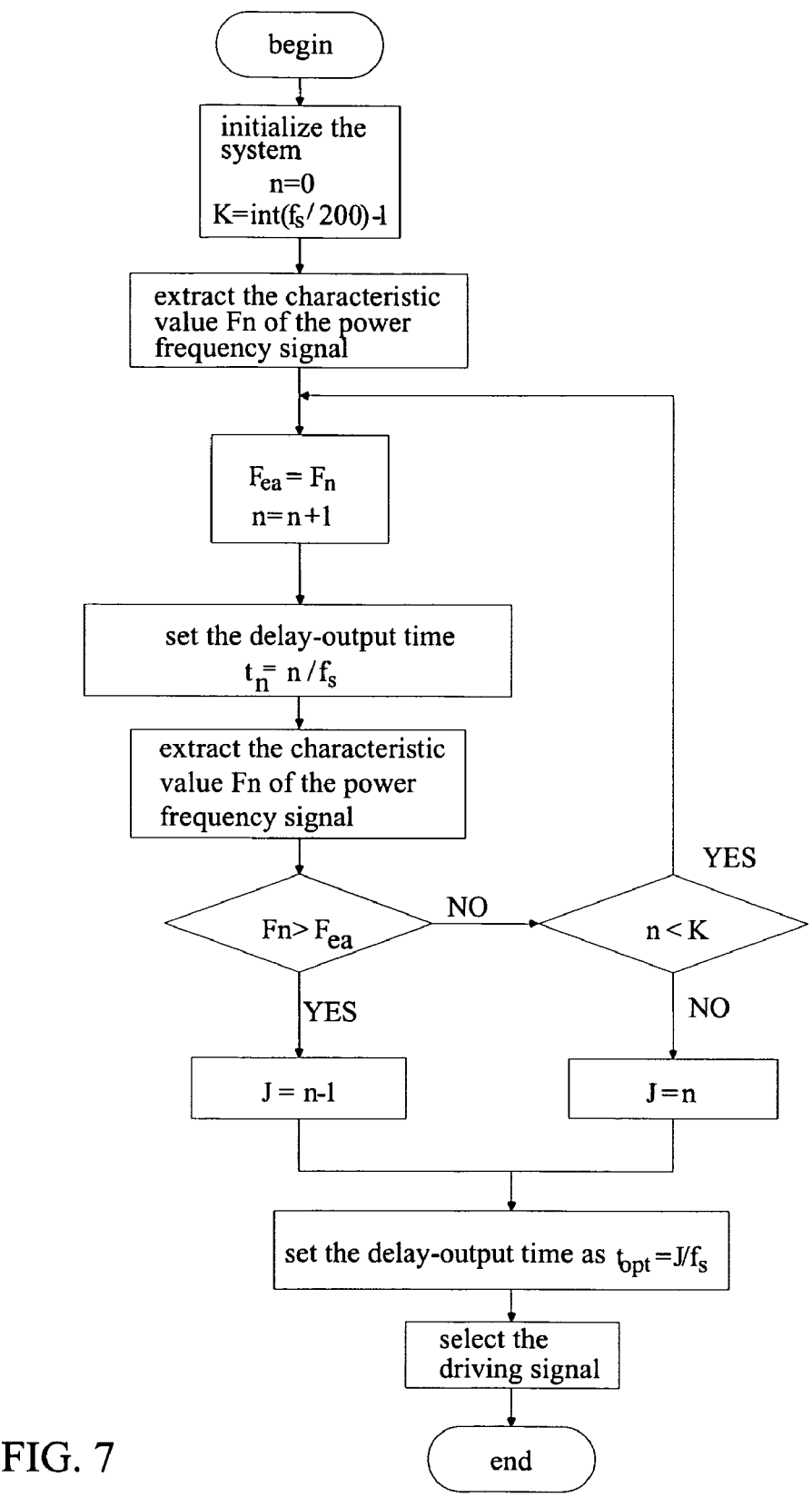
FIG. 7 is a flow chart of the method for suppressing power frequency common mode interference according to the present invention.

In FIG. 7, for the sake of clearness, a variable $F_{ea}$ is used for storing the characteristic value in the current system state. Another characteristic value after the system entering into a next state will be compared with the variable to determine which one is greater. If J denotes a system optimum state value, the intensity of the power frequency interference signals in this optimum state is a local minimum value, and the time for delay output corresponding to the optimum state is $$t_{opt} = \frac{J}{f_s}.$$

Take the ECG signal measuring system with sampling frequency $f_s$=1 kHz as an example, $$K = \text{int}\left(\frac{f_s}{200}\right) - 1 = 4,$$

then n is chosen from [0, 4]. There are five compensating states of the right leg driving circuit within the phase compensation interval of [0, π/2). When n=0, 1, 2, 3, 4, the delay-output time of the right leg driving signal is 0, 1 ms, 2 ms, 3 ms, 4 ms respectively, then the corresponding phase compensation amounts are $$0, \frac{1}{10}\pi, \frac{1}{5}\pi, \frac{3}{10}\pi, \frac{2}{5}\pi.$$

If the characteristic value of the power frequency interference is minimal when n=2, then this state will be regarded as the system optimum state, thus the delay time at this point is set to 2 ms.

The phase compensating and processing means receives the bioelectrical signal in the step B. The sampling can be performed by the A/D converter under the control of the microprocessor, and then a characteristic analysis on sampled data is performed in step C. In the characteristic analysis, the power frequency interference characteristic value may be calculated by following steps of:

a) successively storing data of the bioelectrical signal sampled by the A/D converter into a predetermined data array;
b) receiving the data array by a digital band-pass filter so as to extract the power frequency interference signal and output related data;
c) detecting a maximum value and a minimum value of the output data within a period, so as to calculate the peak to peak value of the signal within the period;
d) calculating a sum of the peak to peak values in a plurality of adjacent periods so as to get the characteristic value $F_n$ of the power frequency interference.

The band-pass filter may be a simple band-pass filter, for example but not limited to, two-order Butterworth band-pass filter with a center frequency of 50 Hz or 60 Hz and a bandwidth of ±2 Hz. It will be not further discussed here, since it is well-known in prior art.

Correspondingly, the step D for performing a corresponding time delay processing on the amplified signal outputted by the driving circuit includes steps of:

D1) controlling the A/D converter by a microprocessor of the phase compensating and processing means, setting a sampling channel and a sampling frequency $f_s$, and sampling the amplified signal outputted by the driving circuit;
D2) creating a data array org_data[K+1], and successively storing amplified signal sampled by the A/D converter;
D3) determining a delay-output datum according to an optimum state value J of the current system, which corresponds an array element org_data[K−J] of the data array;
D4) converting the datum outputted at the sampling frequency $f_s$ into an analog signal by the D/A converter and then outputting the analog signal.

The successively storing means, after each time of A/D conversion, each data originally stored in the array element is stored in another array element located just before the array element, while the array element org_data[K] stores the just sampled data. Other storing method which is equivalent with or transformed from the above manner may be adopted. Further description will be omitted.

The step D in which the signals outputted by the driving circuit is received and a corresponding time delay processing is performed on the signals may employ other processing methods. For example, the driving signal can be output directly via a delayer which is controlled by the microprocessor and the delay time thereof is adjustable, which also falls into the scope of this invention.

The embodiments of this invention is testified by the experiments of human body ECG measurement that the intensity of power frequency interference signals in original ECG signals can be reduced by more than a half once the sampling frequency $f_s$ is 1 kHz. It is indicated from the above analysis that the more accurate delay time and better effect for suppressing power frequency interference can be achieved if higher sampling frequency is adopted.

What is claimed is:

1. An apparatus for suppressing power frequency common mode interference and used in a bioelectrical signal measuring system, comprising:
    a common mode interference signal extracting circuit;
    a driving circuit connected to the extracting circuit, the driving circuit configured to generate a first driving signal; and
    a delayer connected to the driving circuit, the delayer configured to perform a corresponding adjustable time delay on the first driving signal outputted by the driving circuit,
    wherein the driving circuit is further configured to change a phase of a common mode interference signal and amplify the common mode interference signal to generate, the first driving signal, wherein either the first driving signal or a second driving signal comprising a modified version of the first driving signal is selectively outputted to a living body on examination,
    wherein the apparatus further includes phase compensating and processing circuitry configured to:
        receive both a bioelectrical signal from the living body on examination and the first driving signal outputted from the driving circuit,
        determine a phase compensation amount of the first driving signal outputted from the driving circuit according to a characteristic value of a power frequency interference in the bioelectrical signal so as to phase-compensate the first driving signal outputted from the driving circuit to generate the second driving signal, and
        selectively output, based on a user selection, either the first driving signal or the second driving signal to the living body on examination.

2. The apparatus for suppressing power frequency common mode interference as claimed in claim 1, wherein the phase compensating and processing circuitry includes:
    a microprocessor;
    at least one A/D converter configured to convert the bioelectrical signal and the other amplified signal outputted from the driving circuit into digital signals respectively and to supply the digital signals to the microprocessor, wherein the microprocessor is configured to determine the phase compensation amount of the other amplified signal outputted from the driving circuit according to the characteristic value of the power frequency interference in the bioelectrical signal; and
    a D/A converter configured to receive a signal from the microprocessor and to convert the signal into an analog signal.

3. The apparatus for suppressing power frequency common mode interference as claimed in claim 1, wherein the apparatus further includes a low-pass filter, through which the phase-compensated amplified signal outputted by the phase compensating and processing circuitry passes before being transmitted to the living body on examination.

4. The apparatus for suppressing power frequency common mode interference as claimed in claim 1, wherein the apparatus further includes switching and selecting circuitry with two selecting terminals, one of which is connected to an output terminal of the driving circuit, the other of which is connected to an output terminal of the phase compensating and processing circuitry, and wherein the switching and selecting circuitry is configured to selectively output the amplified signal outputted by the driving circuit and the phase-compensated amplified signal outputted by the phase compensating and processing circuitry to the living body on examination.

5. The apparatus for suppressing power frequency common mode interference as claimed in claim 3, wherein the apparatus further includes switching and selecting circuitry with two selecting terminals, one of which is connected to an output terminal of the driving circuit, the other of which is connected to an output terminal of the low-pass filter, and wherein the switching and selecting circuitry is configured to selectively output the amplified signal outputted by the driving circuit and the phase-compensated amplified signal outputted by the phase compensating and processing circuitry to the living body on examination.

6. A method for suppressing power frequency common mode interference, which is used for suppressing interference of power frequency common mode signal as a bioelectrical signal measuring system detects bioelectrical signals, wherein the measuring system comprises a common mode interference signal extracting circuit and a driving circuit connected to the extracting circuit configured to generate a first driving signal by both changing phases of a common mode interference signal and amplifying the common mode interference signal, wherein the method includes steps of:
    A. providing phase compensating and processing circuitry between the driving circuit and a living body on examination;
    B. receiving the first driving signal outputted from the driving circuit and a bioelectrical signal from the living body on examination by the phase compensating and processing circuitry;
    C. analyzing, by the phase compensating and processing circuitry, a characteristic of the bioelectrical signal and determining a phase compensation amount of the first driving signal outputted from the driving circuit, wherein the characteristic of the bioelectrical signal is represented by a characteristic value of a power frequency interference in the bioelectrical signal;
    D. performing, by the phase compensating and processing circuitry, a corresponding time delay processing on the first driving signal outputted by the driving circuit to generate a second driving signal, wherein the first driving signal outputted by the driving circuit is transmitted to a delayer for performing a corresponding time delay processing, which is controlled by a microprocessor and whose delay time is adjustable; and
    E. selectively transmitting, by the phase compensating and processing circuitry, based on a user selection, either the first driving signal or the second driving signal to the living body on examination.

7. The method for suppressing power frequency common mode interference as claimed in claim 6, wherein the step C, as performed by the phase compensating and processing circuitry, includes steps of:
    C1) initializing a system state value of the measuring system;
    C2) extracting a characteristic value of the power frequency interference in a current system state of the measuring system;
    C3) adding 1 to the system state value and extracting another characteristic value again;
    C4) if the another characteristic value being decreased, the decrease in the another characteristic value indicates that the power frequency interference is reduced, thus the direction of the compensation is correct, then continuing the step C3) until the system state value becomes maximized; otherwise, a lack of decrease in the another characteristic value indicates that the direction of the compensation is incorrect, then subtracting 1 from the system state value, and then an optimum system state value is selected, wherein the system state value is integer and corresponds to one phase compensation state; and C5) setting the optimum system state value in the step C4) as a state value of the current system, to determine a corresponding phase compensation amount.

8. The method for suppressing power frequency common mode interference as claimed in claim 7, wherein the system state value ranges from [0, K], in which $$K = \text{int}\left(\frac{f_s}{200}\right) - 1,$$

int( ) denotes a rounding operation, and $f_s$ denotes a sampling frequency of the bioelectrical signal.

9. The method for suppressing power frequency common mode interference as claimed in claim 7, wherein the characteristic value of the power frequency interference refers to a sum of peak to peak values of the power frequency interference signal extracted from the bioelectric signal within a plurality of periods, which is calculated by steps of:

a) successively storing, by the phase compensating and processing circuitry, data of the bioelectrical signal sampled by an A/D converter of the phase compensating and processing circuitry into a predetermined data array in the phase compensating and processing circuitry;

b) processing the data array, by a digital band-pass filter of the phase compensating and processing circuitry, so as to extract the power frequency interference signal and output related data;

c) detecting, by the phase compensating and processing circuitry, a maximum value and a minimum value of the output data within a period, so as to calculate the peak to peak value of the signal within the period; and d) calculating, by the phase compensating and processing circuitry, a sum of the peak to peak values in a plurality of adjacent periods so as to get the characteristic value of the power frequency interference.

10. The method for suppressing power frequency common mode interference as claimed in claim 6, wherein the step D for performing a corresponding time delay processing on the first driving signal outputted by the driving circuit includes steps of:

D1) controlling the A/D converter by a microprocessor of the phase compensating and processing circuitry, setting a sampling channel and a sampling frequency $f_s$, and sampling the first driving signal outputted by the driving circuit;

D2) creating a data array $org_{13}$ data[K+1], and successively storing samples of the first driving signal sampled by the A/D converter;

D3) determining a delay-output datum according to an optimum state value J of the current system, which corresponds an array element $org_{13}$ data[K-J] of the data array;

D4) converting the datum outputted at the sampling frequency $f_s$ into an analog signal by the D/A converter and then outputting the analog signal as the second driving signal; wherein $$K = \text{int}\left(\frac{f_s}{200}\right) - 1,$$

and int ( ) denotes a rounding operation.

* * * * *